United States Patent [19]

Aronchick

[11] Patent Number: 5,616,346
[45] Date of Patent: Apr. 1, 1997

[54] NON-AQUEOUS COLONIC PURGATIVE FORMULATIONS

[76] Inventor: Craig A. Aronchick, 903 Bryn Mawr Ave., Penn Valley, Pa. 19072

[21] Appl. No.: 669,834

[22] Filed: Jun. 26, 1996

Related U.S. Application Data

[63] Continuation of Ser. No. 411,350, Mar. 31, 1995, abandoned, which is a continuation of Ser. No. 64,640, May 18, 1993, abandoned.

[51] Int. Cl.$^6$ .................................................. A61K 33/42
[52] U.S. Cl. ............................................ 424/606; 514/892
[58] Field of Search ............................. 424/606; 514/892

[56] References Cited

U.S. PATENT DOCUMENTS

| | | | |
|---|---|---|---|
| 3,088,870 | 5/1963 | McDermott | 424/602 |
| 3,676,553 | 7/1972 | Reynolds | 424/602 |
| 3,821,368 | 6/1975 | Reynolds | 424/602 |
| 4,432,966 | 2/1984 | Zeitoun | 424/21 |
| 4,452,779 | 6/1984 | Cockerill | 424/601 |
| 4,665,100 | 5/1987 | Ludwig | 514/778 |
| 4,725,427 | 2/1988 | Ashmead et al. | 424/44 |
| 4,812,311 | 3/1989 | Uchtman | 514/167 |
| 4,842,871 | 6/1989 | Hill | 426/44 |
| 4,904,474 | 2/1990 | Theeuwes | 424/424 |
| 5,108,758 | 4/1992 | Allwood | 424/468 |
| 5,124,144 | 6/1992 | Giorgetti | 424/78.01 |

OTHER PUBLICATIONS

A Randomized Prospective Trial Comparing Oral Sodium Phosphate with Standard Polyethylene Glycol–Based Lavage Solution (Golytely) in the Preparation of Patients for Colonoscopy; Vanner, M.D., et. al.; The American Journal of Gastroenterology; vol. 85, No. 4, p. 422; 1990.

Development of a Lavage Solution Associated with Minimal Water and Electrolyte Absorption or Secretion; Davis, et. al.; Gastroenterology 76:991–995, 1980.

Physicians' Desk Reference; pp. 699–700;992–993; & 1826–1827;1992.

Martindale, The Extra Pharmacopoeia, 28$^{th}$ edition (1982) pp. 641–642.

Physician's Desk Reference, 1995 (ed) pp. 608–609.

*Primary Examiner*—Raymond Henley, III
*Attorney, Agent, or Firm*—Robert F. Zielinski

[57] ABSTRACT

Orally administered colonic purgative formulations and methods of its use for effecting partial or complete purgation of the colon in mammals, the formulations consisting of non-aqueous admixtures of monobasic, dibasic and tribasic sodium phosphates administered in tablet or capsule form in concentrations of from 0.01 to 0.85 grams per kilogram body weight. Preferred embodiments include the addition of binders, dispersants and buffers which do not adversely affect osmolality or effectiveness of the purgative formulations.

19 Claims, No Drawings

NON-AQUEOUS COLONIC PURGATIVE FORMULATIONS

This application is a continuation of application Ser. No. 08/411,350, filed Mar. 31, 1995, now abandoned, which is a continuation of application Ser. No. 08/064,640, filed May 18, 1993, now abandoned.

This invention relates to colonic purgative formulations and, more particularly, to nonaqueous purgative formulation compositions which may be administered in capsule or tablet form for preparing the colon for surgical or diagnostic procedures.

BACKGROUND OF THE INVENTION

In order to carry out a number of medical procedures, such as colonoscopy, radiographic examination and in preparation for patients undergoing bowel surgery, it is often critical that the colon be emptied as completely as possible. For example, one of the most essential conditions for obtaining satisfactory radiographs is that the intestines be cleansed sufficiently, particularly with regard to the elimination of gas from the colon. The same condition also applies when the colon is preoperatively prepared for surgery, or for diagnostic procedures such as colonoscopies, in which case it is also necessary to remove fecal waste materials.

In the past, in order to effect an emptying of the colon, water enemas have been previously employed wherein large quantities of water are introduced into the colon to induce emptying; the contents of the colon being expelled in the form of a suspension. It has however been recognized that the introduction of too large a quantity of water in enemas or too frequently administered enemas may be injurious to the patient. In view of the hazard and disadvantages associated with large volume water enemas, it has become know to introduce enemas of a hypertonic aqueous solution typically, of various salts to substitute for the large water enema. The advantage of these salt formulations is that they requires significantly less water volume in their administration. The effect of these hypertonic enemas is based on the increase of the osmotic pressure in the colon which, in turn, may have undesirable side effects, particularly, if the hypertonic solution diffuses through the wall of the colon and disturbs the fluid balance of the body. While an improvement over simple water enemas, this potential side effect limits the utility of these compositions.

Additionally, many enema compositions in aqueous solutions include a contact laxative agent causing peristalsis in the colon with sufficient concentration of laxation without the need for excessive amounts of water. Such compositions often include salt mixtures and may also chemical agents such as propylene glycol and non-ionic wetting agents such as polyether alcohols. The problems with these formulations, aside from the often problematic methods of enema administration, are incomplete evacuation of the bowels often requiring repeated administrations and the inclusion of certain chemicals which may have an irritating effect on the colonic walls. Furthermore, because it is often necessary to employ repeated washout enemas to clear the colon effectively, the potential for such chemical irritation is greatly increased.

More recently, a number of orally administered liquid pharmaceutical compositions have been developed for use as gastrointestinal washes for diagnostic purposes or for use as cathartic laxatives. Such preparations consist of aqueous solutions of polyethylene glycol and electrolytes such as sodium sulfate, sodium bicarbonate, sodium chloride and potassium chloride. These orally administered compositions are particularly useful in the rapid washing of the colon for diagnostic purposes. For example, when a powerful gastrointestinal wash is required, such preparations are generally administered in a quantity of about four liters, the composition being typically formulated according to the following: polyethylene glycol 59 g., sodium sulphate 5.68 g., sodium bicarbonate 1.69 g., sodium chloride 1.46 g., potassium chloride 0.745 g. and water to make up one liter. Laxation and relatively thorough evacuation is often significantly improved over enema formulations, and generally without the problems often encountered with enema administrations.

The advantages of using these preparations over other orally administered preparations are a drastic reduction in wash time (from 3–2 days to 4–5 hours) and the minimization of water and electrolyte losses. The advantages which these types of solutions provide are derived from two essential characteristics of the preparation, namely, its isoosmoticity with the physiological liquids, and the balance of the ion species in solution, so as to compensate the transport mechanisms which regulate gastrointestinal absorption. These characteristics result in substantial isotonicity between the preparation and the intracellular and extracellular fluids at the tissues of the digestive tubes walls.

Commercially available product embodying these formulations typically utilize a polyethylene glycol formula serving as a non-absorbable osmotic agent with a mixture of electrolytes for replenishment, so that patients do not become dehydrated. Patients are required to ingest a significant amount of volume for purgation which may include a one eight ounce glass every ten minutes for a total of one gallon of fluid. Due to the fact that the volume is so high, use of this type of formulation is frequently associated with a tremendous amount of distention and significant amounts of nausea.

Another serious drawback of these know preparations is their decidedly unpleasant, bitter, noticeably saline taste which in the more sensitive patients can lead to vomiting thereby preventing ingestion. However, as the requirement of solution isotonicity is necessary to obtain the aforesaid advantages, the introduction of water soluble adjuvants, for example, to alter taste, must be avoided. Even the most common natural sweeteners such as glucose, fructose, saccharose, and sorbitol could change the osmolarity of these solutions and the inclusion of such adjuvants are generally expressly prohibited. Moreover, even altering the unpleasant taste of these preparations with artificial sweeteners or flavorants in these commercial preparations must be avoided as they could also alter the critical isotonicity.

Furthermore, in the aforesaid preparations of the known art, it is also well recognized that the addition of appreciable quantities of substances which can be fermented by the intestinal flora should be avoided. This is because gas could form which could be extremely dangerous in the case of colonoscopy with electrocautery.

In an attempt to avoid the problems associated with the high volume types of preparations, other investigators have utilized ingestible preparations which consist of aqueous solutions of phosphate salts. The aqueous phosphate salt solution produces a tremendous osmotic effect on the intraluminal contents of the bowel and therefore, evacuation of the bowel occurs with a tremendous increase in the influx of water and electrolytes into the colon. This has been developed for the express purpose of decreasing the volume required in colonic purgations. One such preparation basically is comprised of 480 grams per liter monobasic sodium phosphate and 180 grams per liter dibasic sodium phosphate in stabilized buffered aqueous solution and is sold under the brand name Fleet® Phospho®-Soda. Patients are typically required to take two three ounce dosages of this preparation, separated by a three hour interval for a total of six ounces, which is a significant reduction compared to for the example the 128 ounces required by other high volume preparations.

The major short-coming of such concentrated aqueous phosphate solution administration is however, that the aqueous solution is extremely unpalatable, so much so that the recommended dosage form is administered ice cold so as to minimize the objectionable saline taste. Often patients complain of severe nausea and vomiting, possible secondary to the extremely salty taste of the preparation. Frequently, patients cannot even tolerate the ingestion of this preparation at the initial dose and often the second dose becomes even more problematic due to the unpalatable extremely salty taste, even when the taste is partially masked by the use of flavoring agents. Thus, while concentrated purgation solutions represent a slight improvement over other methods of inducing purgation, the short comings of these solutions are readily apparent.

From the foregoing, it can be seen that it is desirable to have an orally administered colonic purgative formulation which may be easily and conveniently administered and which avoids the problems and objectionable tastes of known formulations. It can also be seen that it is desirable to have such a purgative formulation which may be administered without large volumes of water necessary in conventional formulations and which avoids other potentially irritant chemicals or chemicals which could effect osmolality.

It is an object of the present invention to provide an easily and conveniently administered dosage formulation of an effective colonic purgative.

It is also an object of the present invention to provide such a formulation which may be used as a purgative or as a laxative according to the dosage formulation.

It is yet another object of the present invention to provide a colonic purgative formulation which avoids the unpleasant salty taste of such know formulation.

It is still another object of the present invention to provide a method of administering a colonic purgative with a minimum amount of patient discomfort.

Yet another objective of the instant invention is to provide a formulation for colonic purgatives which avoids the addition of other components which may be broken down by intestinal flora.

These and other objects and advantages of the invention will be evident after reading the following description.

BRIEF SUMMARY OF THE INVENTION

The present invention relates to a colonic purgative formulation in which are contained pharmaceutically active amounts of sodium phosphate salts in a stable, nonaqueous tablet dosage form. In one preferred embodiment, the dosage formulation comprises a mixture of monobasic sodium phosphate and dibasic sodium phosphate. In this embodiment, the formulation is an admixture of approximately 0.4 to 0.85 grams per kilogram body weight of monobasic sodium phosphate and 0.1 to 0.5 grams per kilogram body weight dibasic sodium phosphate which may be conveniently administered to the patient in a tablet or capsule form. Preferably the patient dosage is 0.62 grams per kilogram body weight of monobasic sodium phosphate and 0.23 grams per kilogram body weight dibasic sodium phosphate.

In other preferred embodiments, the formulation may be predominately or exclusively dibasic sodium phosphate within the above ranges and may further include tablet binders, dispersants and/or buffering agents. Further, in other preferred embodiments, the formulation may include tribasic sodium phosphate in addition to either monobasic or dibasic sodium phosphate, or both, within the above ranges.

DETAILED DESCRIPTION OF THE INVENTION

The physiology of intestinal secretion and absorption is generally well known as reflected in the reported literature. It is quite clear that intestinal absorption of sodium and water occurs largely in the small intestine. Approximately nine liters of gastrointestinal fluid is produced per day from the saliva, stomach, liver, pancreas and proximal small intestine and all but one to one and one half liters is reabsorbed by the small intestine before this passes the ileo-cecal valve into the colon. The colon the efficiently reabsorbs approximately 80% of the residual fluids culminating into a normal stool output of approximately 200 milliliters per day. The majority of sodium and water reabsorbed by the jejunum is due to the high permeability of the membranes of the cells of the small intestine along with active sodium pumping from the cell into the interstitial fluid, culminating eventually into absorption into the capillary system. The net flux of sodium and water from the lumen into the blood is dependent upon many different factors. For example, changes in the intra-luminal osmolality of the proximal intestinal contents will promote a decrease in reabsorption of sodium and water and a net secretion of water into the lumen, ultimately producing diarrhea. As the osmolality of intra-luminal fluid increases, this produces a transmucosal flux of water from the capillary and interstitial fluid into the lumen in an effort to produce isotonicity. This tremendous flux of water that occurs with highly osmolar intra-luminal substances brings along with it sodium via a solvent drag phenomenon, thusly, which increases intra-luminal water to tremendous degrees. The amount of intra-luminal water increases directly proportional to the osmolality of the intra-luminal fluid. Applicant's invention is believed to function by creating an increase in intra-luminal fluid of the small bowel to a significant degree allowing for a net secretion of sodium and water into the lumen, and thus allowing for tremendous fluxes of water to be present within the gastrointestinal lumen, producing a purgative effect.

In a preferred embodiment, Applicant's invention consists of a dry admixture of monobasic and dibasic sodium phosphates in an anhydrous state. One hundred grams of the formulation may be prepared by combining approximately 70–73% weight of pharmaceutical grade anhydrous monobasic sodium phosphate with approximately 26–30% weight of pharmaceutical grade anhydrous dibasic sodium phosphate in a ribbon blender or other similar mixing apparatus to effect complete mixing of the components. Additional constituents such as tablet binders, dispersants and/or buffering agents in the range of approximately 1 to 4% weight, may also be included in the admixture.

In other preferred embodiments, the amount of monobasic sodium phosphate may be substantially reduced or eliminated in its entirety. In these formulations, dibasic sodium phosphate or tribasic sodium phosphate may be used alone or in combination as the principal or exclusive form of phosphate in the formulation, while maintaining complete purgative effect. Upon ingestion, phosphate salts cause a tremendous amount of water to be drawn into the gut. This influx of water causes an increase in intraluminal pressure, which in turn exerts a mechanical stimulus causing an increase in intestinal motility. The purgative effect of the phosphate salts appears to be proportionately related to the increase in the anionic state of the phosphate salt and may be differentiated in their mode of action from other salt formulations which are capable of producing a limited cathartic effect. One such salt, magnesium sulfate, for example, exerts its effect via the magnesium cation which causes hypermotility of the gut.

The admixture is formed into an easily administered dosage form, such as tablets or into capsules by methods well known in the art. As used herein, the term admixture refers to a formulation which includes at least one phosphate salt and at least one other component including other phosphate salts or other additives as disclosed herein. When forming tablets containing the purgative formulation, it will be appreciated that the salts can be compressed into a uniform mixture and can optionally include inert diluents such as a tablet binder. Preferably, the tablet binder is a pharmaceutically acceptable binder and is one which produces no appreciable osmotic effects. Examples of useful binders include non-ionic detergents such as Pluronic F-68 (a trademark of BASF-Wyandotte Chemicals, defined as a condensate of ethylene oxide with a condensate of propylene oxide and propylene glycol) and mechanical adhesives such as polyvinyl alcohol and sodium carboxymethylcellulose. Microcrystalline cellulose (MCC) may also be used to enhance the compactability of the phosphate salts into the tablet or capsule form.

In another preferred embodiment of the instant invention, the tablet or capsules may also include inert dispersal agents which will facilitate dissolution of the tablet or capsule contents in the stomach of the patient. Preferably, the dispersal agent is a pharmaceutically acceptable dispersant and is one which also produces no appreciable osmotic effects. Examples of acceptable dispersants include microcrystalline cellulose (which is also useful as a compacting agent) and anhydrous lactose. A preferred dispersal agent is AC-DI-SOL, a cross-linked starch.

In another preferred embodiment of the present invention, the preferred composition may also include a buffering agent to minimize any acid imbalance which may accompany ingestion of the purgative formulation of Applicant's invention. Suitable buffering agents include magnesium hydroxide, aluminum hydroxide, calcium carbonate and magnesium carbonate.

An important characteristic of the colonic purgative formulations of the instant invention is that they function effectively as purgatives when administered in low volume dosages, as compared to known formulations. In this manner, 5 to 12 tablets, and preferably 7 to 10 tables per dose, depending on tablet size and weight, with only fluids necessary to assist in swallowing the tablets, will provide complete purgation. The dosage may be administered in a single application but is preferably administered in two applications separated by approximately 2 to 4 hours. Use of the formulations of this invention in tablet form effectively removes the colonic contents without requiring injestion of large quantities of water. Conventional purgative products historically and currently available on the market have had to employ much greater liquid volumes in order to obtain the desired result.

Another important characteristic of the instant formulations is that at lower dosages they will function effectively as laxatives. Concentration ranges for laxative effect are from approximately 0.025 to 0.1 grams/kg body wt. and preferably are from 0.05 to 0.07 grams/kg body wt.

The foregoing description is illustrative of the preferred embodiments shown. It is not intended to limit the present invention to the specific formulations shown and described, but instead it will be appreciated that adaptations and modifications will become apparent from the present disclosure and are intended to be within the scope of the claims.

What I claim is:

1. An orally administrable composition capable of dispersal in the stomach for inducing purgation of the colon in humans consisting essentially of an effective colonic purgative amount of at least one sodium phosphate salt wherein said composition is in a non-aqueous form selected from the group consisting of tablets and gelatin capsules and wherein one or more additives selected from the group consisting of buffering agents, dispersal agents and binding agents are optionally present.

2. The composition in claim 1 wherein said sodium phosphate salt is monobasic sodium phosphate and further wherein the concentration of said salt is from approximately 70 to 73 percent by weight.

3. The composition of claim 1 wherein said sodium phosphate salt is dibasic sodium phosphate and further wherein the concentration of said salt is from approximately 26 to 30 percent by weight.

4. The composition of claim 1 wherein said sodium phosphate salt is a mixture of monobasic sodium phosphate in a concentration range from approximately 70 to 73 percent by weight and dibasic sodium phosphate in a concentration range from approximately 26 to 30 percent by weight.

5. The composition of claim 1 wherein said sodium phosphate salt is a mixture of monobasic sodium phosphate, dibasic sodium phosphate and tribasic sodium phosphate.

6. The composition of claim 5 wherein a buffering agent is present and is selected from the group consisting of magnesium hydroxide, aluminum hydroxide, calcium carbonate and magnesium carbonate.

7. The composition of claim 5 wherein a buffering agent is present and is selected from the group consisting of anhydrous lactose, microcrystalline cellulose and AC-DI-SOL.

8. The composition of claim 5 wherein a buffering agent is present and is selected from the group consisting of non-ionic detergents, mechanical adhesives and microcrystalline cellulose.

9. A method of inducing purgation in the colon of humans comprising the steps of:

(a) preparing a non-aqueous mixture consisting essentially of at least one sodium phosphate salt to form a purgative formulation;

(b) forming an orally administrable, dry dosage form of said purgative formulation;

(c) orally administering a pharmaceutically effective amount of said formulation to a human without dispersing said dry dosage form into water prior to administration; and (d) allowing said administered dry dosage form to induce purgation.

10. The method of claim 9 wherein step (a) further includes the step of adding to said purgative formulation at least one member selected from the group consisting of buffering agents, dispersal agents and binders.

11. The method of claim 9 wherein said orally administrable dosage form is selected from the group consisting of gelatin capsules and tablets.

12. The method of claim 9 wherein the admixture formed in step (a) includes monobasic sodium phosphate and dibasic phosphate.

13. The method of claim 12 wherein said monobasic sodium phosphate is administered at rate of from about 0.4 grams per kilogram body weight to 0.85 grams per kilogram body weight.

14. The method of claim 12 Wherein said dibasic sodium phosphate is administered at a rate of from about 0.1 grams per kilogram body weight to 0.5 grams per kilogram body weight.

15. The method of claim 9 wherein said sodium phosphate salt is tribasic sodium phosphate.

16. The method of claim 9 wherein said sodium phosphate salt is dibasic sodium phosphate and at least one member selected from the group consisting of monobasic sodium phosphate and tribasic sodium phosphate.

17. A method of inducing purgation of the colon in mammals comprising the steps of:

(a) preparing a non-aqueous admixture of approximately 72% by weight monobasic and approximately 26% by weight dibasic sodium phosphate salts to form a purgative formulation;

(b) forming orally administrable tablets of said purgative formulation;

(c) orally administering said tablets to said mammal at a rate of from 0.1 to 0.5 grams per kilogram body weight of dibasic sodium phosphate; and (d) allowing said administered dosage to induce purgation.

18. The method of claim 17 wherein step (c) is repeated at least once.

19. An orally administrable, nonaqueous composition capable of dispersal within the stomach for inducing purgation in the colon of humans comprising an effective colonic purgative amount of approximately 70 to 73% monobasic sodium phosphate, approximately 26 to 30% dibasic sodium phosphate and approximately 1 to 4% inert additives selected from the group consisting of tablet binders, dispersants and buffering agents, wherein said composition is in a form selected from the group consisting of tablets and gelatin capsules.

* * * * *